(12) United States Patent
Addison et al.

(10) Patent No.: US 9,770,210 B2
(45) Date of Patent: Sep. 26, 2017

(54) SYSTEMS AND METHODS FOR ANALYZING A PHYSIOLOGICAL SENSOR SIGNAL

(75) Inventors: Paul S. Addison, Midlothian (GB); James Watson, Fife (GB)

(73) Assignee: NELLCOR PURITAN BENNETT IRELAND, Mervue, Galway (IE)

( * ) Notice: Subject to any disclaimer, the term of this patent is extended or adjusted under 35 U.S.C. 154(b) by 1198 days.

(21) Appl. No.: 13/243,619

(22) Filed: Sep. 23, 2011

(65) Prior Publication Data
US 2013/0079601 A1 Mar. 28, 2013

(51) Int. Cl.
*A61B 5/00* (2006.01)
*A61B 5/1455* (2006.01)

(52) U.S. Cl.
CPC ........ *A61B 5/7221* (2013.01); *A61B 5/14551* (2013.01)

(58) Field of Classification Search
None
See application file for complete search history.

(56) References Cited

U.S. PATENT DOCUMENTS

| | | | |
|---|---|---|---|
| 4,819,752 A | 4/1989 | Zelin | |
| 4,863,265 A | 9/1989 | Flower et al. | |
| 5,351,685 A | 10/1994 | Potratz | |
| 5,533,507 A | 7/1996 | Potratz | |
| 5,553,615 A * | 9/1996 | Carim et al. | 600/324 |
| 5,577,500 A | 11/1996 | Potratz | |
| 5,755,226 A * | 5/1998 | Carim et al. | 600/323 |
| 5,803,910 A | 9/1998 | Potratz | |
| 5,921,921 A | 7/1999 | Potratz et al. | |
| 5,995,858 A | 11/1999 | Kinast | |

(Continued)

FOREIGN PATENT DOCUMENTS

| | | |
|---|---|---|
| JP | 6098881 | 4/1994 |
| JP | 2004159810 | 6/2004 |

(Continued)

OTHER PUBLICATIONS

Ayres et al. Schaum's Outline of Theory and Problems of Differential and Integral Calculus Third Edition Copyright 1990, 1962 by the McGraw-Hill Companies, Inc.*

(Continued)

*Primary Examiner* — William Thomson
*Assistant Examiner* — Shirley Jian
(74) *Attorney, Agent, or Firm* — Fletcher Yoder PC

(57) ABSTRACT

The present disclosure relates generally to patient monitoring systems and, more particularly, to signal analysis for patient monitoring systems. In one embodiment, a method of analyzing a detector signal of a physiological patient sensor includes obtaining the detector signal from the physiological patient sensor, wherein the detector signal crosses a horizontal boundary more than once. The method also includes determining the relative time and the slope of the detector signal at each boundary crossing. The method further includes estimating the amplitude of the detector signal based, at least in part, on the determined relative time and slope of the detector signal at each boundary crossing. The method also includes determining a physiological parameter of a patient based, at least in part, on the estimate of the amplitude of the detector signal.

13 Claims, 6 Drawing Sheets

(56) References Cited

U.S. PATENT DOCUMENTS

| | | | |
|---|---|---|---|
| 6,381,479 B1 | 4/2002 | Norris | |
| 7,003,338 B2 | 2/2006 | Weber et al. | |
| 7,003,339 B2 | 2/2006 | Diab et al. | |
| 7,209,775 B2 | 4/2007 | Bae et al. | |
| 7,215,984 B2 | 5/2007 | Diab et al. | |
| 7,215,986 B2 | 5/2007 | Diab et al. | |
| 7,221,971 B2 | 5/2007 | Diab et al. | |
| 7,227,640 B2 | 6/2007 | Ochiai | |
| 7,254,433 B2 | 8/2007 | Diab et al. | |
| 7,302,284 B2 | 11/2007 | Baker, Jr. et al. | |
| 7,315,753 B2 | 1/2008 | Baker, Jr. et al. | |
| 7,328,053 B1 | 2/2008 | Diab et al. | |
| 7,336,983 B2 | 2/2008 | Baker, Jr. et al. | |
| 7,376,453 B1 | 5/2008 | Diab et al. | |
| 7,383,070 B2 | 6/2008 | Diab et al. | |
| 7,544,168 B2 * | 6/2009 | Nitzan | 600/495 |
| 8,150,510 B2 * | 4/2012 | Swerdlow | 607/7 |
| 8,321,017 B2 * | 11/2012 | Wenzel | A61B 5/0215 607/18 |
| 8,512,240 B1 * | 8/2013 | Zuckerman-Stark et al. | 600/301 |
| 9,066,679 B2 * | 6/2015 | Beach | A61B 5/02007 |
| 2005/0113656 A1 | 5/2005 | Chance | |
| 2005/0143634 A1 | 6/2005 | Baker, Jr. et al. | |
| 2005/0209517 A1 | 9/2005 | Diab et al. | |
| 2006/0074322 A1 * | 4/2006 | Nitzan | 600/485 |
| 2006/0161057 A1 | 7/2006 | Weber et al. | |
| 2006/0217609 A1 | 9/2006 | Diab et al. | |
| 2007/0149872 A1 | 6/2007 | Zhang et al. | |
| 2007/0225582 A1 | 9/2007 | Diab et al. | |
| 2007/0249918 A1 | 10/2007 | Diab et al. | |
| 2007/0291832 A1 | 12/2007 | Diab et al. | |
| 2008/0004514 A1 | 1/2008 | Diab et al. | |
| 2008/0033265 A1 | 2/2008 | Diab et al. | |
| 2008/0033266 A1 | 2/2008 | Diab et al. | |
| 2008/0033494 A1 * | 2/2008 | Swerdlow | 607/5 |
| 2008/0036752 A1 | 2/2008 | Diab et al. | |
| 2008/0045823 A1 | 2/2008 | Diab et al. | |
| 2011/0316704 A1 * | 12/2011 | Nielsen et al. | 340/573.1 |

FOREIGN PATENT DOCUMENTS

| | | |
|---|---|---|
| JP | 2005095581 | 4/2005 |
| WO | WO9309711 | 5/1993 |
| WO | WO9842249 | 10/1998 |
| WO | WO9842251 | 10/1998 |

OTHER PUBLICATIONS

Aoyagi, T., et al.; "Analysis of Motion Artifacts in Pulse Oximetry," Japanese Society ME, vol. 42, p. 20 (1993) (Article in Japanese—contains English summary of article).

Barreto, A.B., et al.; "Adaptive Cancelation of Motion artifact in Photoplethysmographic Blood Volume Pulse Measurements for Exercise Evaluation," IEEE-EMBC and CMBEC—Theme 4: Signal Processing, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," Journal of clinical Monitoring, vol. 13, pp. 109-113 (1997).

Barnum, P.T., et al.; "Novel Pulse Oximetry Technology Capable of Reliable Bradycardia Monitoring in the Neonate," Respiratory Care, vol. 42, No. 1, p. 1072 (Nov. 1997).

Poets, C. F., et al.; "Detection of movement artifact in recorded pulse oximeter saturation," Eur. J. Pediatr.; vol. 156, pp. 808-811 (1997).

Masin, Donald I., et al.; "Fetal Transmission Pulse Oximetry," Proceedings 19th International Conference IEEE/EMBS, Oct. 30-Nov. 2, 1997; pp. 2326-2329.

Leahy, Martin J., et al.; "Sensor Validation in Biomedical Applications," IFAC Modelling and Control in Biomedical Systems, Warwick, UK; pp. 221-226 (1997).

Barreto, Armando B., et al.; "Adaptive LMS Delay Measurement in dual Blood Volume Pulse Signals for Non-Invasive Monitoring," IEEE, pp. 117-120 (1997).

East, Christine E., et al.; "Fetal Oxygen Saturation and Uterine Contractions During Labor," American Journal of Perinatology, vol. 15, No. 6, pp. 345-349 (Jun. 1998).

Hayes, Matthew J., et al.; "Quantitative evaluation of photoplethysmographic artifact reduction for pulse oximetry," SPIE, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An in-Vitro Investigation," Proceedings of the 20th Annual International conference of the IEEE Engie in Medicine and Biology Society, vol. 20, No. 6, p. 3072-3075, 1998.

Hayes, Matthew J., et al.; "Artifact reduction in photoplethysmography," Applied Optics, vol. 37, No. 31, pp. 7437-7446 (Nov. 1998).

Such, Hans Olaf; "Optoelectronic Non-invasive Vascular Diagnostics Using multiple Wavelength and Imaging Approach," Dissertation, (1998) 40 pages.

Todd, Bryan, et al.; "The Identification of Peaks in Physiological Signals," Computers and Biomedical Research, vol. 32, pp. 322-335 (1999).

Rhee, Sokwoo, et al.; "Design of a Artifact-Free Wearable Plethysmographic Sensor," Proceedings of the First joint BMES/EMBS Conference, Oct. 13-16, 1999, Altanta, Georgia, p. 786.

Rheineck-Leyssius, Aart t., et al.; "Advanced Pulse Oximeter Signal Processing Technology Compared to Simple Averaging: I. Effect on Frequency of Alarms in the Operating Room," Journal of clinical Anestesia, vol. 11, pp. 192-195 (1999).

Kaestle, S.; "An Algorithm for Reliable Processing of Pulse Oximetry Signals Under strong Noise Conditions," Dissertation Book, Lubeck University, Germany (1999) 13 pages.

Goldman, Julian M.; "Masimo Signal Extraction Pulse Oximetry," Journal of Clinical Monitoring and Computing, vol. 16, pp. 475-483 (2000).

Coetzee, Frans M.; "Noise-Resistant Pulse Oximetry Using a Synthetic Reference Signal," IEEE Transactions on Biomedical Engineering, vol. 47, No. 8, Aug. 2000, pp. 1018-1026.

Yao, Jianchu, et al.; "Design of a Plug-and-Play Pulse Oximeter," Proceedings of the Second Joint EMBS/BMES Conference, Houston, Texas, Oct. 23-26, 2002; pp. 1752-1753.

Kaestle, S.; "Determining Artefact Sensitivity of New Pulse Oximeters in Laboratory Using Signals Obtained from Patient," Biomedizinische Technik, vol. 45 (2000) 14 pages.

Cysewska-Sobusaik, Anna; "Metrological Problems With noninvasive Transillumination of Living Tissues," Proceedings of SPIE, vol. 4515, pp. 15-24 (2001).

Belal, Suliman Yousef, et al.; "A fuzzy system for detecting distorted plethysmogram pulses in neonates and paediatric patients," Physiol. Meas., vol. 22, pp. 397-412 (2001).

Hayes, Matthew J., et al.; "A New Method for Pulse Oximetry Possessing Inherent Insensitivity to Artifact," IEEE Transactions on Biomedical Engineering, vol. 48, No. 4, pp. 452-461 (Apr. 2001).

Gehring, Harmut, et al.; "The Effects of Motion Artifact and Low Perfusion on the Performance of a New Generation of Pulse Oximeters in Volunteers Undergoing Hypoxemia," Respiratory Care, vol. 47, No. 1, pp. 48-60 (Jan. 2002).

Jopling, Michae W., et al.; "Issues in the Laboratory Evaluation of Pulse Oximeter Performance," Anesth Analg, vol. 94, pp. S62-S68 (2002).

Gostt, R., et al.; "Pulse Oximetry Artifact Recognition Algorithm for Computerized Anaesthetic Records," Journal of Clinical Monitoring and Computing Abstracts, p. 471 (2002).

Chan, K.W., et al.; "17.3: Adaptive Reduction of Motion Artifact from Photoplethysmographic Recordings using a Variable Step-Size LMS Filter," IEEE, pp. 1343-1346 (2002).

(56) References Cited

OTHER PUBLICATIONS

Yamaya, Yoshiki, et al.; "Validity of pulse oximetry during maximal exercise in normoxia, hypoxia, and hyperoxia," J. Appl. Physiol., vol. 92, pp. 162-168 (2002).

Tremper, K.K.; "A Second Generation Technique for Evaluating Accuracy and Reliability of Second Generation Pulse Oximeters," Journal of Clinical Monitoring and Computing, vol. 16, pp. 473-474 (2000).

Cyrill, D., et al.; "Adaptive Comb Filter for Quasi-Periodic Physiologic Signals," Proceedings of the 25th Annual International Conference of the IEEE EMBS, Cancun, Mexico, Sep. 17-21, 2003; pp. 2439-2442.

Stetson, Paul F.; "Determining Heart Rate from Noisey Pulse Oximeter Signals Using Fuzzy Logic,". The IEEE International Conference on Fuzzy Systems, St. Louis, Missouri, May 25-28, 2003; pp. 1053-1058.

Aoyagi, Takuo; "Pulse oximetry: its invention, theory, and future," Journal of Anesthesia, vol. 17, pp. 259-266 (2003).

Lee, C.M. et al.; "Reduction of motion artifacts from photoplethysmographic recordings using wavelet denoising approach," IEEE EMBS Asian-Pacific Conference on Biomedical Engineering, Oct. 20-22, 2003; pp. 194-195.

A. Johansson; "Neural network for photoplethysmographic respiratory rate monitoring," Medical & Biological Engineering & Computing, vol. 41, pp. 242-248 (2003).

Addison, Paul S., et al.; "A novel time-frequency-based 3D Lissajous figure method and its application to the determination of oxygen saturation from the photoplethysmogram," Institute of Physic Publishing, Meas. Sci. Technol., vol. 15, pp. L15-L18 (2004).

Yao, Jianchu, et al.; "A Novel Algorithm to Separate Motion Artifacts from Photoplethysmographic Signals Obtained With a Reflectance Pulse Oximeter," Proceedings of the 26th Annual International conference of the IEEE EMBS, San Francisco, California, Sep. 2004, pp. 2153-2156.

Matsuzawa, Y., et al.; "Pulse Oximeter," Home Care Medicine, pp. 42-45 (Jul. 2004); (Article in Japanese—contains English summary of article).

Yan, Yong-sheng, et al.; "Reduction of motion artifact in pulse oximetry by smoothed pseudo Wigner-Ville distribution," Journal of NeuroEngineering and Rehabilitation, vol. 2, No. 3. 9 pages, Mar. 2005.

Huang, J., et al.; "Low Power Motion Tolerant Pulse Oximetry," Abstracts, A7, p. S103 (undated).

P. Lang, et al.; "Signal Identification and Quality Indicator™ for Motion Resistant Pulse Oximetry," Abstracts, A10, p. S105 (undated).

Hamilton, Patrick S., et al.; "Effect of Adaptive Motion-Artifact Reduction on QRS Detection," Biomedical Instrumentation & Technology, pp. 197-202 (undated).

Kim, J.M., et al.; "Signal Processing Using Fourier & Wavelet Transform," pp. II-310-II-311 (undated).

Odagiri, Y.; "Pulse Wave Measuring Device," Micromechatronics, vol. 42, No. 3, pp. 6-11 (undated) (Article in Japanese—contains English summary of article).

Yamazaki, Nakaji, et al.; "Motion Artifact Resistant Pulse Oximeter (Durapulse PA 2100)," Journal of Oral Cavity Medicine, vol. 69, No. 4, pp. 53 (date unknown) (Article in Japanese—contains English summary of article).

Maletras, Francois-Xavier, et al.; "Construction and calibration of a new design of Fiber Optic Respiratory Plethysmograph (FORP)," Optomechanical Design and Engineering, Proceedings of SPIE, vol. 4444, pp. 285-293 (2001).

Relente, A.R., et al.; "Characterization and Adaptive Filtering of Motion Artifacts in Pulse Oximetry using Accelerometers," Proceedings of the Second joint EMBS/BMES Conference, Houston, Texas, Oct. 23-26, 2002; pp. 1769-1770.

Neumann, R., et al.; "Fourier Artifact suppression Technology Provides Reliable SpO2," Abstracts, A11, p. S105 (undated).

\* cited by examiner

SYSTEMS AND METHODS FOR ANALYZING A PHYSIOLOGICAL SENSOR SIGNAL

BACKGROUND

The present disclosure relates generally to patient monitoring systems and, more particularly, to signal analysis for patient monitoring systems.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors routinely desire to monitor certain physiological characteristics of their patients. Accordingly, a wide variety of systems and devices have been developed for monitoring many of these physiological characteristics. Generally, these patient monitoring systems provide doctors and other healthcare personnel with the information they need to provide the best possible healthcare for their patients. Consequently, such monitoring systems have become an indispensable part of modern medicine.

In general, these patient monitoring systems may include a patient sensor that has a detector (e.g., an optical or electrical detector) that is configured to perform a measurement on the tissue of a patient. In pulse oximetry, for example, it is desirable to determine the signal amplitude and periodicity to determine physiological parameters, such as the oxygen level of the patient's blood and the patient's pulse rate. However, the signal produced by the detector may suffer from various types of noise (e.g., electrical noise, interference, artifacts from patient activity, etc.). Such noise in a detector signal may introduce substantial complexity as well as possible inaccuracy into the determination of the physiological parameter of the patient. For example, it may be difficult to determine the amplitude or strength of a noisy signal. As such, if a signal includes a substantial amount of noise it may be difficult to accurately calculate the physiological parameter of the patient using conventional methods. Additionally, it may be difficult to determine the level of noise present within a detector signal to determine the quality of the detector signal.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
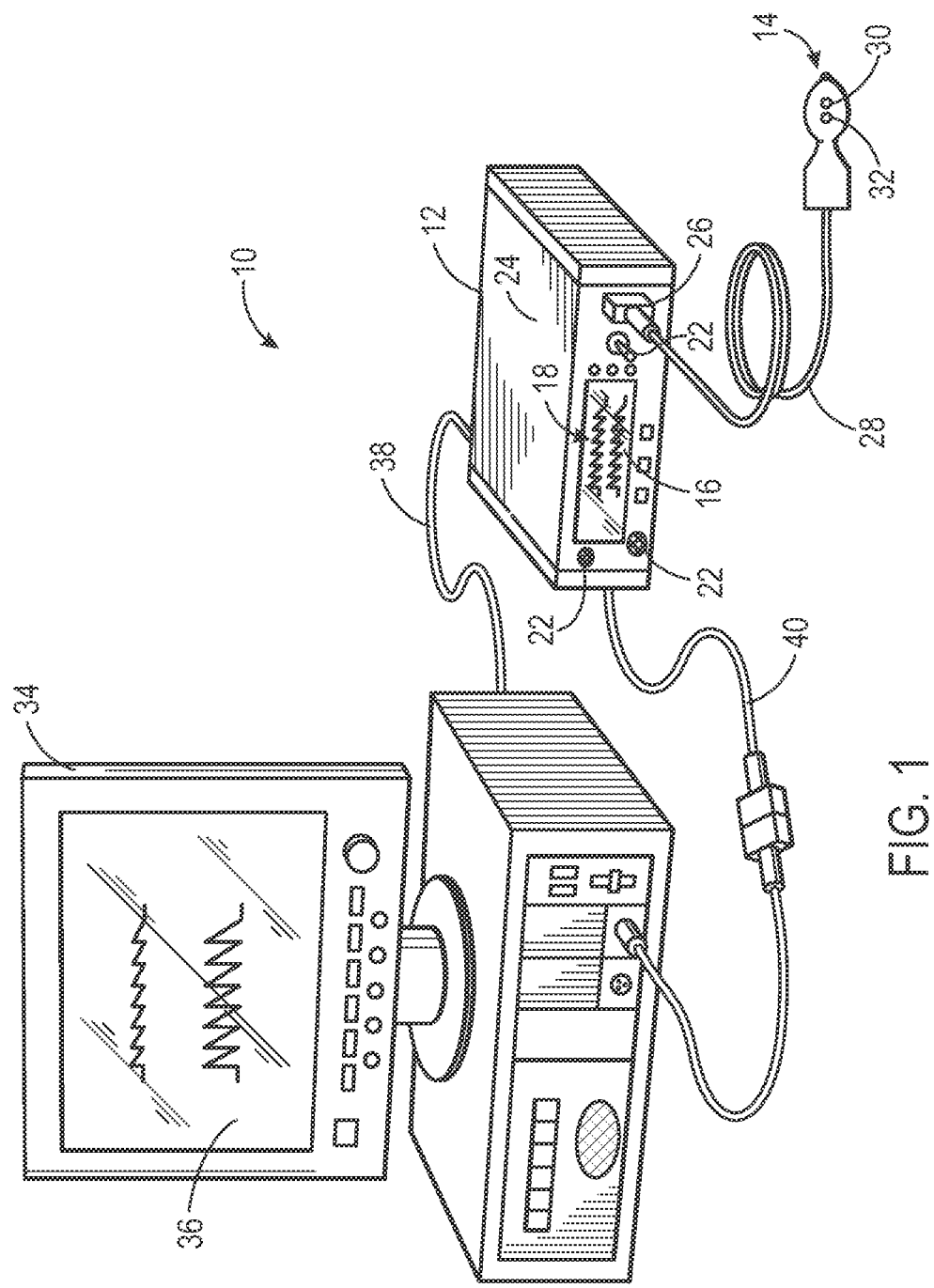
FIG. 1 illustrates a perspective view of a pulse oximeter, in accordance with an embodiment of the present disclosure.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

It should be noted that the term "signal amplitude," as used herein, refers to the strength of the detector signal. Additionally, the "slope" or "gradient" of the detector signal at a particular point refers to the gradient or slope of a line tangent to the detector signal at the particular point, which is mathematically equivalent to the derivative of the detector signal at the particular point.

As mentioned above, the signal from a detector of a patient monitoring system may suffer from a number of types of noise (e.g., electrical interference, artifacts from patient activity, and similar types of noise). Calculating the physiological parameter of a patient using a noisy detector signal is typically computationally challenging and may consume considerable processing resources while potentially producing erroneous results. Accordingly, one feature of the present disclosure is the ability to determine the level of noise present within a detector signal in an efficient manner using fewer processing and memory resources. That is, the present disclosure enables the assessment the quality of a detector signal based on information about the intersections of the detector signal with a horizontal line or boundary (e.g., the horizontal axis). Furthermore, the present disclosure enables the estimation of certain features of the detector signal using other features of the detector signal. That is, the present disclosure enables the estimation of features that may, at times, be difficult to measure (e.g., signal amplitude) based upon other features of the detector signal that are more easily determined (e.g., information about the intersections of the detector signal with a horizontal line or boundary). In particular, the present disclosure enables the estimation of the amplitude or strength of a detector signal based on when the detector signal crosses a horizontal boundary (e.g., the horizontal axis) and the slope of the detector signal at each of these crossings. As such, this estimation of signal amplitude may be used to determine the physiological parameter of the patient in an efficient manner using relatively limited resources (e.g., small buffer size, low-power processor, etc.).

With the foregoing in mind, FIG. 1 illustrates a perspective view of a patient monitoring system 10 that may utilize the presently disclosed detector signal processing algorithms in order to assess the quality of a detector signal and/or estimate the amplitude of the detector signal. The patient monitoring system may be a pulse oximetry monitoring system 10, which monitors the oxygen saturation level of a patient. The patient monitoring system 10 may include a monitor 12, such as those available from Nellcor Puritan Bennett LLC, as well as a sensor 14. The monitor 12 may be configured to display measured and calculated parameters on a display 16. As illustrated, the display 16 may be integrated into the monitor 12. The display 16 may be configured to display computed physiological data including, for example, an oxygen saturation percentage (e.g., $SpO_2$ percentage), a pulse rate, and/or a plethysmographic waveform 18. The monitor 12 may also display information related to alarms, monitor settings, and/or signal quality via indicator lights 20. To further facilitate user input, the monitor 12 may include a plurality of control inputs 22. The control inputs 22 may include fixed function keys, programmable function keys, a touch screen, and soft keys. The control inputs may allow the user to adjust operational parameters of the patient monitoring system 10, such as calibrating sensors or adjusting coefficients used in the calculation of the patient's physiological characteristics. The monitor 12 may also include a casing 24 that may aid in the protection of the internal elements of the monitor 12 from damage.

The monitor 12 may further include a sensor port 26. The monitor 12 may allow for connection to the patient sensor 14 via cable 28, which connects to the sensor port 26. Alternatively, in certain embodiments, a wireless transmission device may be utilized instead of (or in addition to) the cable 28. Furthermore, the sensor 14 may be of a disposable or a non-disposable type and may include a flexible substrate to allow the sensor 14 to conform to the patient. The sensor 14 also includes an emitter 30 configured to emit one or more wavelengths of light into the tissue of the patient and toward a detector 32, which in turn detects light passing through, reflected, or fluoresced by the patient's tissue and produces a corresponding electrical signal. The patient monitor 12 may be configured to calculate physiological parameters received from the sensor 14 relating to this light detection. For example, the sensor 14 may obtain readings from a patient, which can be used by the monitor to calculate certain physiological characteristics, such as the blood-oxygen saturation of hemoglobin in arterial blood, a measure of a patient's dehydration, the volume of individual blood pulsations supplying the tissue, and/or the rate of blood pulsations corresponding to each heartbeat of a patient.

In certain circumstances, it may be useful for a medical professional to have various physiological parameters of the patient collected and displayed in one location. Accordingly, the patient monitoring system 10 may include a multi-parameter patient monitor 34, such as a computer or similar processing-relating equipment. The multi-parameter patient monitor 34 may be generally configured to calculate physiological parameters of the patient and to provide a display 36 for information from the patient monitoring system 10, in addition to other medical monitoring devices or systems. In the present context, the multi-parameter patient monitor 34 may allow a user to address the patient monitor 12, for example, to adjust operational parameters or manage alerts. Additionally, the central display 36 may allow the user to, for example, view current settings, view real-time spectra, view alarms, etc. for the patient monitoring system 10 or other connected medical monitoring devices and systems. The monitor 12 may be communicatively coupled to the multi-parameter patient monitor 34 via a cable 38 or 40 and coupled to a sensor input port or a digital communications port, respectively. In addition, the monitor 12 and/or the multi-parameter patient monitor 34 may be connected to a network to enable the sharing of information with servers or other workstations.

Figure 2:
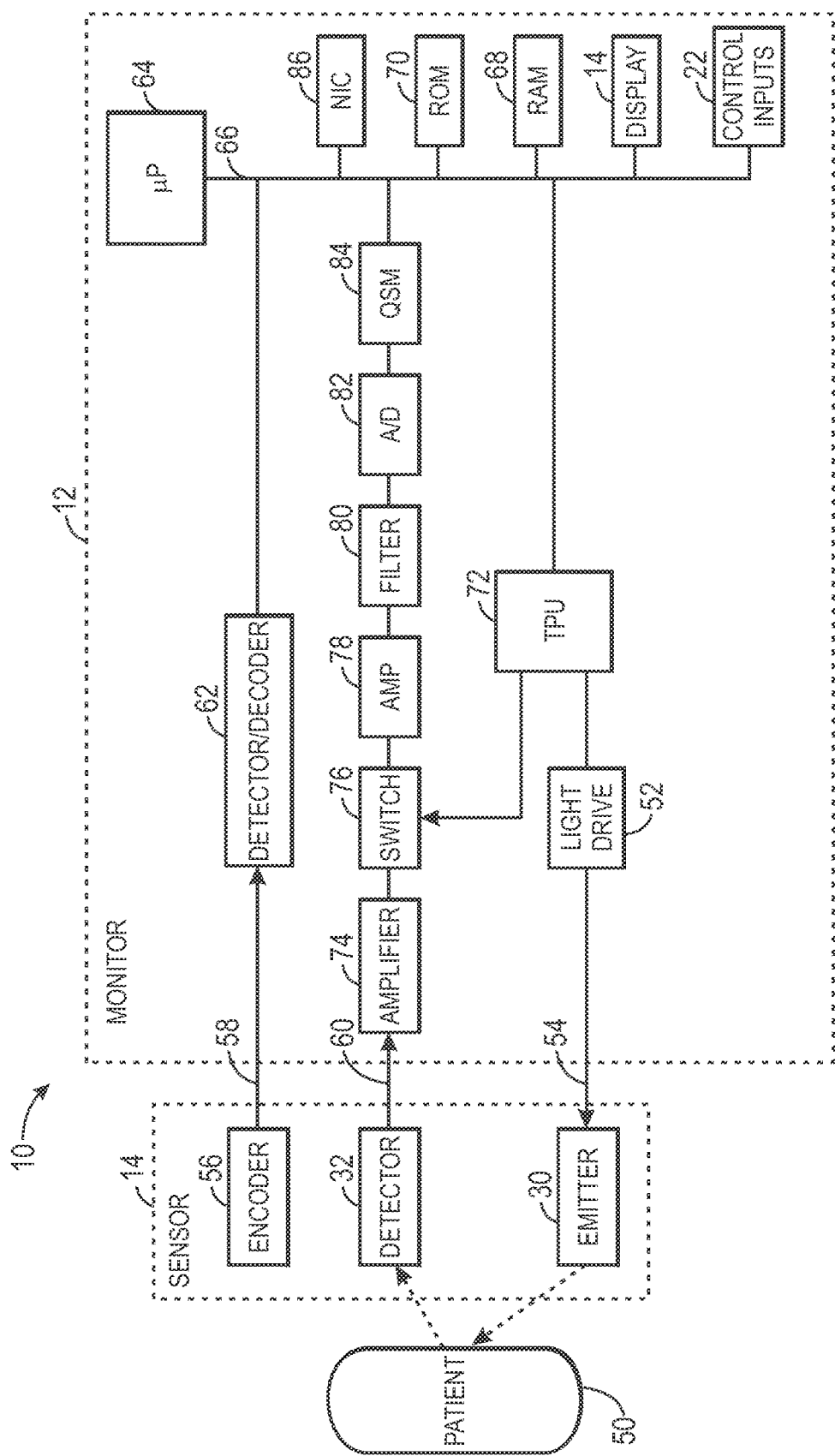
FIG. 2 illustrates a simplified block diagram of a pulse oximeter, in accordance with an embodiment of the present disclosure.

In general, the patient sensor 14 includes a number of components that cooperate with a number of components of the patient monitor 12 to determine one or more physiological parameters of a patient. More specifically, turning to FIG. 2, a simplified block diagram of a patient monitoring system 10 illustrates certain components of the sensor 14 and the monitor 12. The illustrated sensor 14 includes an emitter 30 and a detector 32. The emitter 30 may be capable of emitting light into the tissue of a patient 50 so that the physiological characteristics of the patient 50 may be determined. The light emitted by an emitter 30 may be used to measure, for example, blood oxygenation levels, pulse rat; water fractions, hematocrit, or other physiologic parameters of the patient 50. It should be understood that, as used herein, the term "light" may refer to one or more of ultrasound, radio, microwave, millimeter wave, infrared (IR), visible, ultraviolet (UV), gamma-ray or X-ray electromagnetic radiation, and may also include any wavelength within the radio, microwave, IR, visible, UV, or X-ray spectra, and that any suitable wavelength of light may be appropriate for use with the present disclosure.

The emitter 30 may generally be capable of emitting multiple wavelengths of light (e.g., through the use of multiple LEDs). For example, an emitter 30 for a pulse oximetry sensor 14 may include two LEDs: one LED emitting RED light (e.g., wavelength between about 600 to 700 nm), the other LED emitting infrared (IR) light (e.g., wavelength between about 800 to 1000 nm). The illustrated emitter 30 is controlled by the light drive 52 of the monitor 12 via the emitter line 54. In another embodiment, the light may alternatively be produced by the light drive 52 inside the monitor 12 and subsequently transmitted to the emitter 30, for example, using one or more fiber-optic cables as the emitter line 54.

Additionally, the sensor 14 may include encoder 56 containing encoded information about the sensor 14. For example, such information may include the sensor type (e.g., whether the sensor is intended for placement on a forehead, digit, earlobe, etc.), the number and organization of detectors 32 and emitters 30 present on the sensor 14, the wavelengths of light emitted by the emitter 30, and/or calibration coefficients or calibration curve data to be used in the calculation of the physiological parameter. The information provided by the encoder 56 may be supplied to the monitor 12 (e.g., via the encoder signal line 58) and may indicate to the monitor 12 how to interface with and control the operation of sensor 14, as well as how data is to be exchanged and interpreted. For example, the encoder 56 may supply the monitor 12 with information regarding the control and data lines (e.g. lines 54 or 60) between the monitor 12 and the sensor 14, in addition to the types and ranges of signals that may be transmitted via these communication lines during operation of the system 10. The encoder 56 may also provide information to allow the monitor 12 to select appropriate algorithms and/or calibration coefficients for calculating the physiological characteristics of the patient 50. In certain embodiments, the encoder 56 may, for instance, be implemented as a memory on which the described sensor information may be stored. In one embodiment, the data or signal from the encoder 56 may be decoded by a detector/decoder 62 in the monitor 12, and the detector/decoder 62 may be coupled to the processor 64 via the internal bus 66 of the monitor 12. Additionally, each of the lines coupling the patient monitor 12 to the patient sensor 14 in the illustrated embodiment may represent one or more channels, wires, or cables. In some embodiments, the illustrated lines (e.g., lines 58, 60, and 54) may be bundled together into a single cable (e.g., cable 28) coupling the sensor 14 to the monitor 12.

The patient monitor 12 may include one or more processors 64 coupled to an internal bus 66 and generally controlling the operations of the patient monitoring system 10. The illustrated monitor 12 includes random access memory (RAM) 68, read only memory (ROM) 70, control inputs 22, and a display 14 attached to the internal bus 66. Additionally, a time processing unit (TPU) 72 may also be connected to the bus and may provide timing control signals to light drive circuitry 52 that may control the emitter 30 as described above. The light drive 52 may, for example, use a timing control signal from the TPU 72 to time the activation of an emitter 30 or different light sources (e.g., LEDs) within an emitter 30.

The TPU 72 may also control the gating-in of signals from the sensor 14 (via the signal input line 60) through an amplifier 74 and a switch 76. The incoming signals from the sensor may accordingly be sampled at specific times that may be correlated (at least in part) with the activities of the emitter 30. In the illustrated embodiment, the signal received from the sensor 14 is subsequently passed through a second amplifier 78, a low pass filter 80, and an analog-to-digital converter 82 to amplify, filter, and digitize the electrical signals, respectively. The digital signal data may then be stored in a queued serial module (QSM) 84, for later downloading to RAM 68 as the QSM 84 fills up. The control inputs 22 may also be coupled to the internal bus 66 of the monitor 12 such that monitor parameters set or adjusted using the control inputs 22 may be applied in the operation of the patient monitoring system 10. Additionally, some embodiments of the monitor 12 may also include a network interface card 86, wired or wireless, that may interface with the internal bus 66 of the monitor 12 and allow the transmission of data and/or control signals between a computer network and the monitor 12.

In an embodiment, based at least in part upon the received signals corresponding to the light received by the detector 32, the processor 64 may calculate, for example, the oxygen saturation of the patient 50 using various algorithms. These algorithms may use particular coefficients, which may be empirically determined and stored on the sensor 14 or monitor 12. For example, algorithms relating to the distance between the emitter 30 and the detector 32 may be stored in the monitor (e.g., in ROM 70) or in the sensor (e.g., in the encoder 56) and accessed and operated according to the instructions of the processor 64. For example, in the case of a pulse oximetry patient monitoring system 10, NV memory 44 may include algorithms that calculate a $SpO_2$ value using a ratio-of-ratios calculation, in which the $SpO_2$ value is equal to the ratio of the time-variant (AC) and the time-invariant (DC) components of the detector signal acquired using RED light divided by the ratio of the AC and DC components of the detector signal acquired using IR light.

Figure 3:
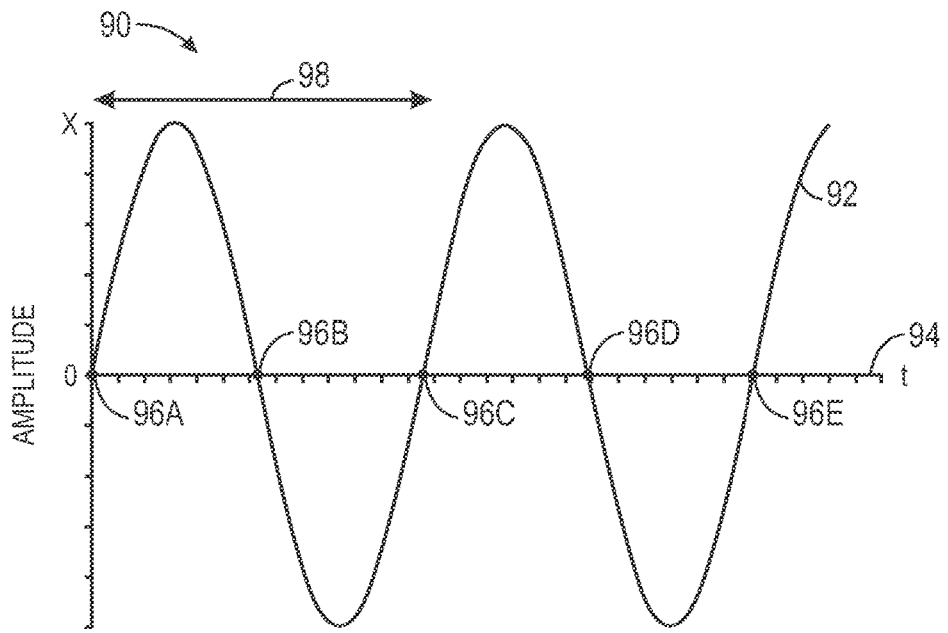
FIG. 3 illustrates an example of a detector signal, in accordance with an embodiment of the present disclosure.

For such a calculation, the AC component of the detector signal may be determined via the application of a low-pass filter to the original detector signal. For example, FIG. 3 illustrates a graph 90 of the AC component of a sinusoidal detector signal 92, x, over time, t. It should be noted that while measuring such a detector signal 92 as a physiological signal from an actual patient may be unlikely, the detector signal 92 provides a simplified example for presenting the present technique and is, therefore, provided for illustrative purposes. With the foregoing in mind, the illustrated detector signal may be described by the following equation:

$$x(t) = A \sin(2\pi f t) \qquad \text{Eq. 1}$$

where A is the amplitude, and f is the frequency. The illustrated portion of detector signal 92 crosses a horizontal boundary (i.e., the horizontal axis 94 or zero-boundary) a number of times (e.g., crossings 96A, 96B, 96C, 96D, 96E) such that the detector signal 92 has a period 98, p, wherein p=1/f. As such, the gradient (or derivative) of the detector signal, may be described by the following equation:

$$\frac{dx}{dt} = x' = A 2\pi f \cos(2\pi f t) \qquad \text{Eq. 2}$$

As such, at the horizontal axis crossings illustrated in FIG. 3, (e.g., 96A-E), the slope, $x'_0$, may either equal $2A\pi f$ or $-2A\pi f$, or, in other words the magnitude of the slope at of the detector signal 92 at the points 96A-E may be defined by the following equation:

$$|x'_0| = 2A\pi f \qquad \text{Eq. 3}$$

As such, the equations may be rearranged to produce the following equation describing the amplitude in terms of the magnitude of the gradient and the period of the crossings:

$$A = \frac{1}{2\pi} |x'_0| P \qquad \text{Eq. 4}$$

As may be noted from Eq. 4 that, generally speaking, as the period, P, of the detector signal 92 increases, the amplitude, A, of the signal increases. Similarly, generally speaking, as the magnitude of the slope of the detector signal 92 (i.e., $|x'_0|$) at the horizontal axis 94 increases, the amplitude, A, of the signal also increases.

Figure 4:
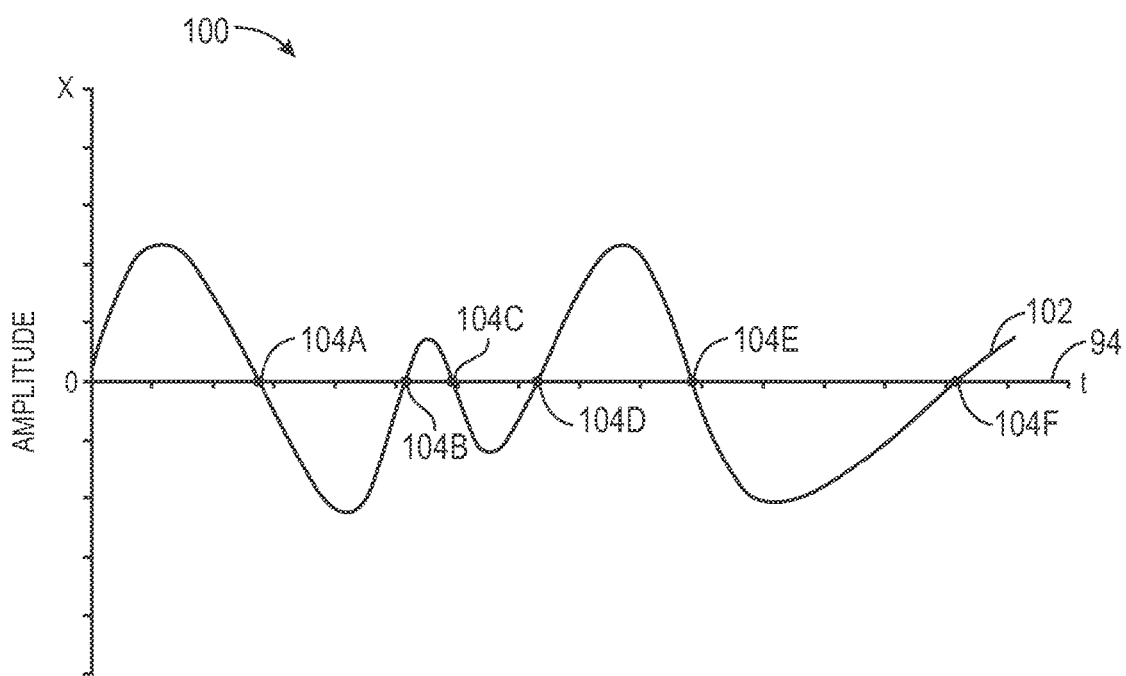
FIG. 4 illustrates another example of a detector signal, in accordance with an embodiment of the present disclosure.

Therefore, while the equation of a typical measured detector signal may not be known, these general trends described above may still be applied. That is, the amplitude of the detector signal may be estimated based on the slope of the detector signal at the horizontal axis and the periodicity of the detector signal. For example, FIG. 4 illustrates a plot 100 of a detector signal 102, which may be a plethysmograph from a patient monitoring system 10. Accordingly, applying the general trends observed above, it may be estimated that as the amount of time between crossing the horizontal axis 94 (e.g., an estimation of the period) increases, the magnitude of the amplitude increases. For example, in comparing the portion of the detector signal between crossings 104B and 104C to the portion of the detector signal between crossings 104D and 104E, as the time between horizontal crossings roughly triples, so does the corresponding amplitude. Similarly, as the magnitude of the slope of the detector signal 102 at the horizontal axis 94 increases, the magnitude of the amplitude also increases. For example, in comparing the portions of the detector signal between crossings 104A and 104B to the portion of the detector signal between crossings 104E and 104F, the slope of the detector signal at 104F is roughly half the magnitude of the slope at 104C. Furthermore, it takes roughly twice as long for the detector signal to go from crossing 104E to 104F that it does to go from 104A to 104B. As such, the two effects generally cancel and the portions of the detector signal 102 between crossings 104A and 104B and between crossings 104E and 104F are roughly equal in amplitude.

Figure 5:
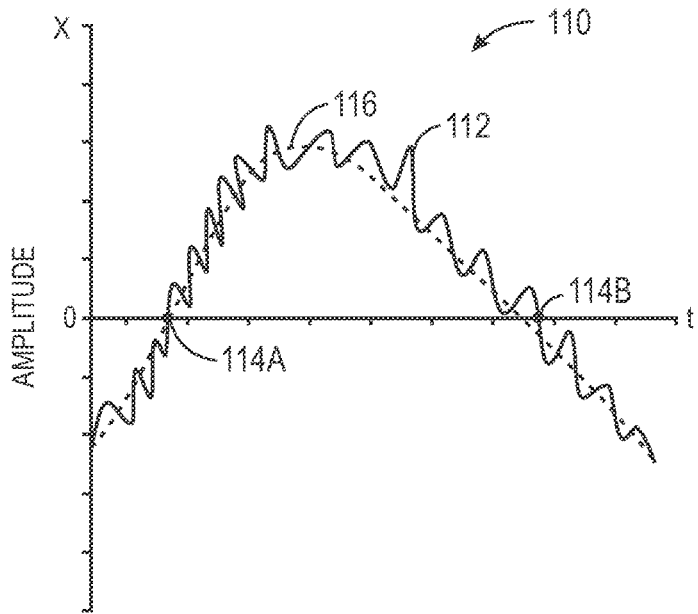
FIG. 5 is a graph illustrating a noisy detector signal, in accordance with an embodiment of the present disclosure.

One advantage of estimating the amplitude of the detector signal based on the intersections of the detector signal and a horizontal boundary (e.g., the horizontal axis) is that signals suffering from certain types of noise (e.g., high frequency noise) may be processed more efficiently. For example, FIG. 5 illustrates a plot 110 of a noisy detector signal 112. For such a noisy signal 112, by relying on the slope of the detector signal 112 when crossing the horizontal axis 94 (e.g., crossings 114A and 114B) and the time between the crossings, a reasonable estimate of the amplitude 116 of the signal 112 may be attained. It should be appreciated that the present technique is also beneficial for signal problems other than noise. For example, if a detector becomes completely saturated (e.g., producing the maximum signal possible and no longer responsive to additional stimulus) during the course of the measurement, then the detector may not be able to measure the amplitude of the detector curve (e.g., at the local maxima). Accordingly, the present technique may enable the patient monitoring system to estimate the amplitude of the detector signal based on measurements that are within the range of the detector (e.g., the information of the intersections of the detector signal with the horizontal axis). It should also be appreciated that in some embodiments, the present signal processing technique may be used in combination with any other signal processing algorithms and techniques (e.g., noise cancelling, noise filtering, curve smoothing, and similar techniques) as commonly known in the art.

Figure 6:
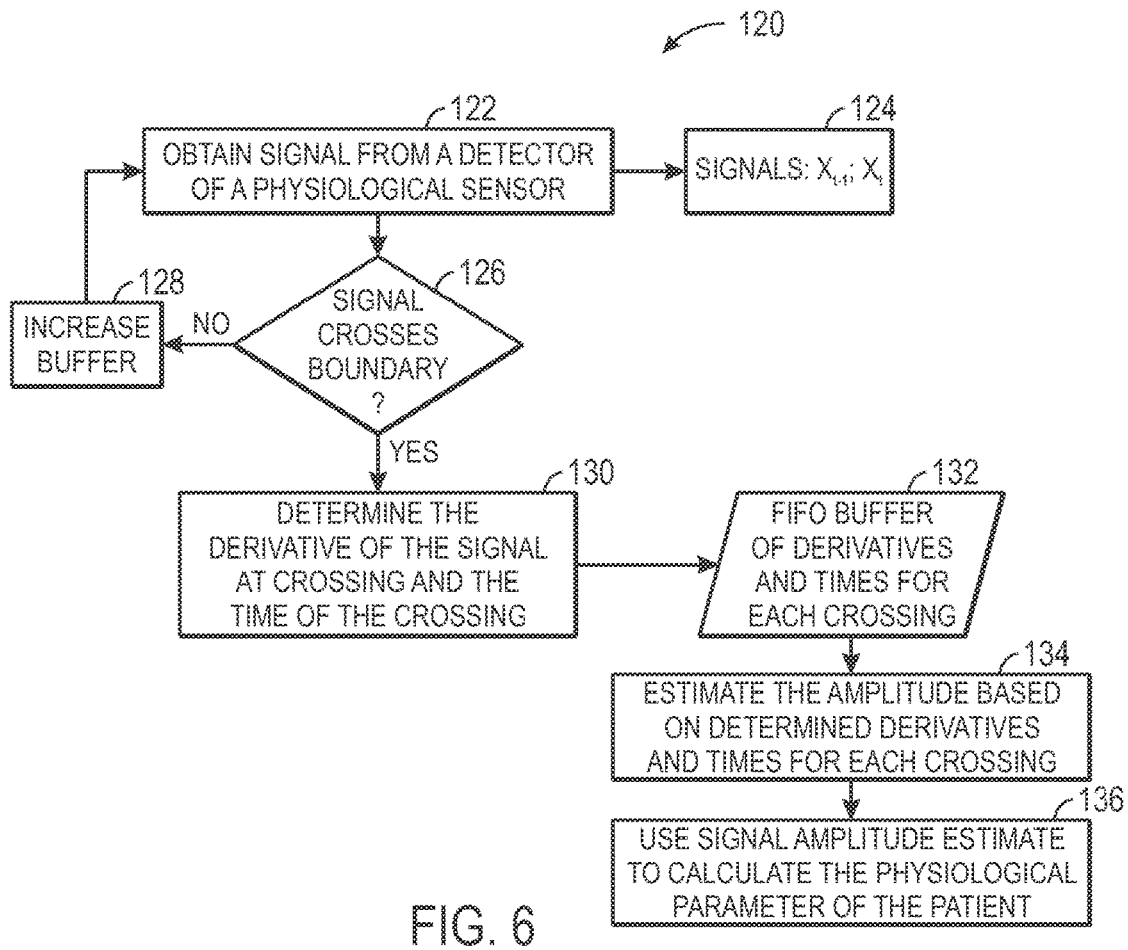
FIG. 6 illustrates a method for estimating the amplitude of a detector signal, in accordance with an embodiment of the present disclosure.

Another advantage of estimating the amplitude of the signal based upon the intersections of the detector signal and a horizontal boundary (e.g., the horizontal axis) is that signal processing may be performed with fewer resources (e.g., less memory and/or less processing power). For example, FIG. 6 is a flow diagram illustrating a process 120 by which a processor (e.g., processor 64) may determine the physiological parameter of a patient using signals measured by a physiological sensor. Accordingly, the process may begin with the processor 64 obtaining signals from the physiological sensor (block 122). The data points $X_{t-1}$ and $X_t$ (block 124) may be collected and stored in a buffer (e.g., in RAM 68). The processor 64 may then determine if the detector signal has crossed the horizontal boundary (e.g., the horizontal axis) between $X_{t-1}$ and $X_t$ (block 126). If not, the processor 64 may increase the buffer size (block 128) and resume collecting data points (block 122). If the detector signal has crossed the boundary, the processor 64 may determine the derivative of the signal at the crossing and the time of the crossing (block 130). Accordingly, in certain embodiments, the processor 64 may subtract $X_{t-1}$ from $X_t$ to determine the derivative of the signal at the crossing. Accordingly, as the processor 64 determines the derivative and the time for each zero crossing, the processor 64 may store the pairs of values in another buffer (e.g., a first-in-first-out (FIFO) buffer in RAM 68).

As such, while the portion of the process 120 described above supplies data to the buffer of block 132, the remainder of the process 120 consumes the data from the buffer. That is, the processor 64 may consume the pairs of data (e.g., derivative at the boundary crossing and time at the zero crossing) in order to estimate the amplitude of the detector signal (block 134). Accordingly, in certain implementations, a processor (e.g., processor 64) may calculate an estimate for the amplitude a portion of a detector signal based on the intersections of the detector signal with the a horizontal boundary (e.g., the horizontal axis). That is, in certain embodiments, the processor 64 may estimate the amplitude of a portion of the detector signal by multiplying the mean, absolute values of the slopes of two adjacent crossings by the period of time between the crossings. In other embodiments, additional constants or terms may be introduced to the calculation to improve the accuracy of the calculation. To further illustrate how an estimate of the detector signal amplitude may be calculated based upon the determined slopes and periods, Appendix A of the present disclosure includes one embodiment of a module (i.e., zerograd.m) demonstrating how the estimate may be calculated by a processor 64. Additionally, in certain implementations, such an estimate may be performed by the processor 64 using a probabilistic or stochastic method (e.g., using non-parametric Bayesian estimates or neural networks). Furthermore, in certain embodiments, the processor 64 may utilize an adaptive rule-based system where logic (e.g., propositional, predicate calculus, Modal, non-monotonic, or fuzzy logic) may define the analytic algorithm or function for estimating the amplitude of the detector signal. Subsequently, the processor 64 may use these signal amplitude estimates to calculate a physiological parameter of the patient (block 136).

Figure 7:
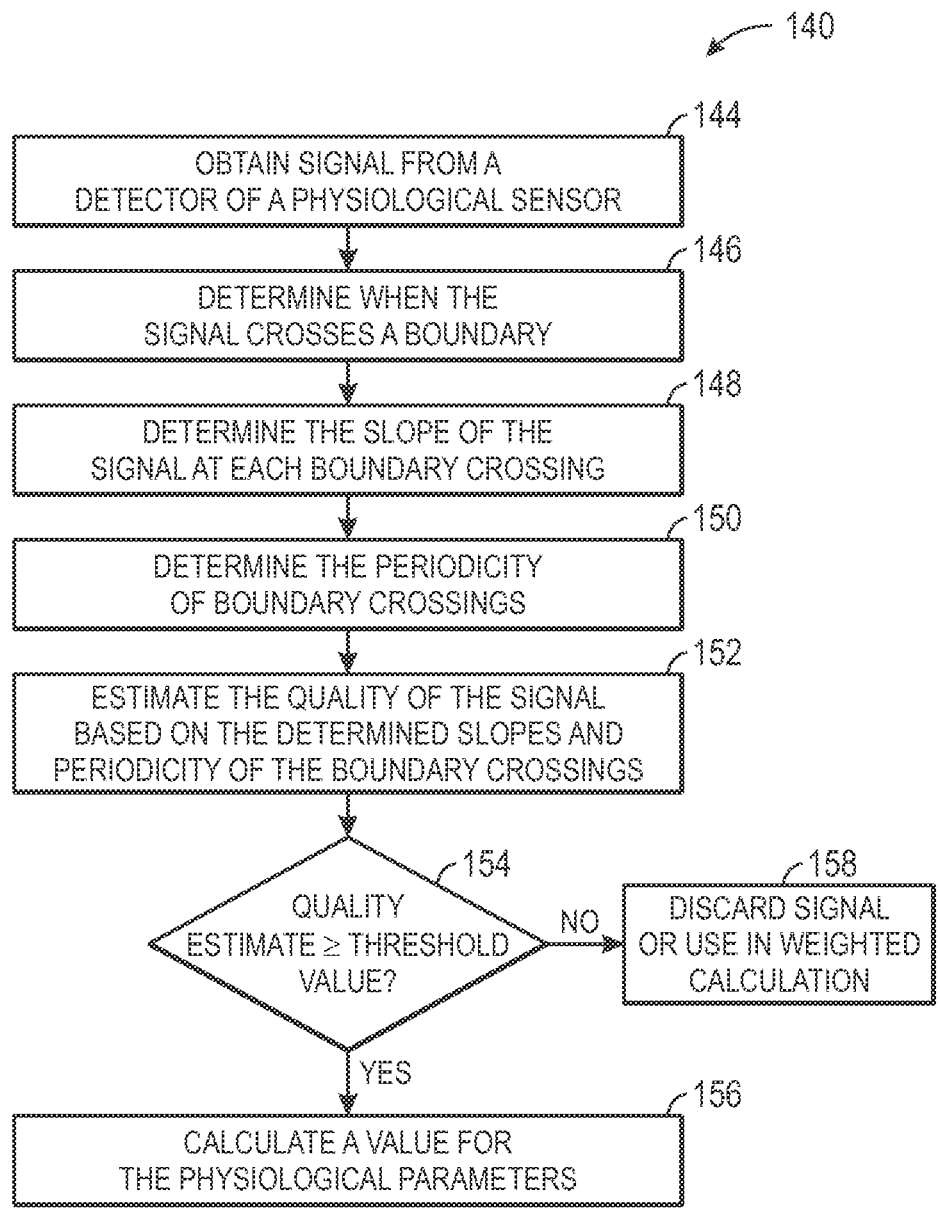
FIG. 7 illustrates a method for determining the quality of a detector signal, in accordance with an embodiment of the present disclosure.

Additionally, the certain embodiments of the present technique may also be used to estimate the quality of a detector signal using relatively less memory and processing resources. For example, FIG. 7 is a flow diagram illustrating one embodiment of a process 140 by which a processor (e.g., processor 64) may determine the quality of a detector signal so that noisy signals may be used differently. The process 140 begins with the processor 64 obtaining a detector signal from a physiological sensor (block 144). The processor 64 may then determine when the detector signal crosses a horizontal boundary (e.g., block 146). In certain embodiments, the boundary may be zero (i.e., the horizontal axis), while in other embodiments, the boundary may be any horizontal line (e.g., x=1, 3, 5, 10, etc.). The processor 64 may determine information regarding the boundary crossings. In particular, the processor 64 may determine the slope of the detector signal at each boundary crossing (block 148) and the periodicity of the boundary crossings (block 150). Based, at least in part, on the determined slopes and periodicity values, the processor 64 may determine an estimate of the quality of the signal (block 152). For example, in certain embodiments, the processor 64 may determine this estimate using a probabilistic or adaptive rule-base system (e.g., a neural network, an expert system, or similar adaptive learning algorithm) where, generally speaking, signals having large slopes at the boundary, short periods, or both are less preferred to signals having average slopes at the boundary and average periods. After determining the signal quality estimate, the processor 64 may then compare the signal quality estimate to a threshold value (block 154). The threshold value may be selected such that only signals that are sufficiently noise free are used to calculate a value for the physiological parameter of the patient (block 156). Accordingly, if the signal quality estimate is below the threshold value, the processor 64 may choose to discard the signal (or some portion thereof) or use the detector signal in a weighted calculation so that the error introduced to the calculation of the physiological parameter of the patient may be mitigated (block 158). In certain embodiments, the information determined regarding the intersections of the detector signal and the boundary may be used to estimate the amplitude of the detector signal in the subsequent determination of the physiological parameter of the patient.

Figure 8:
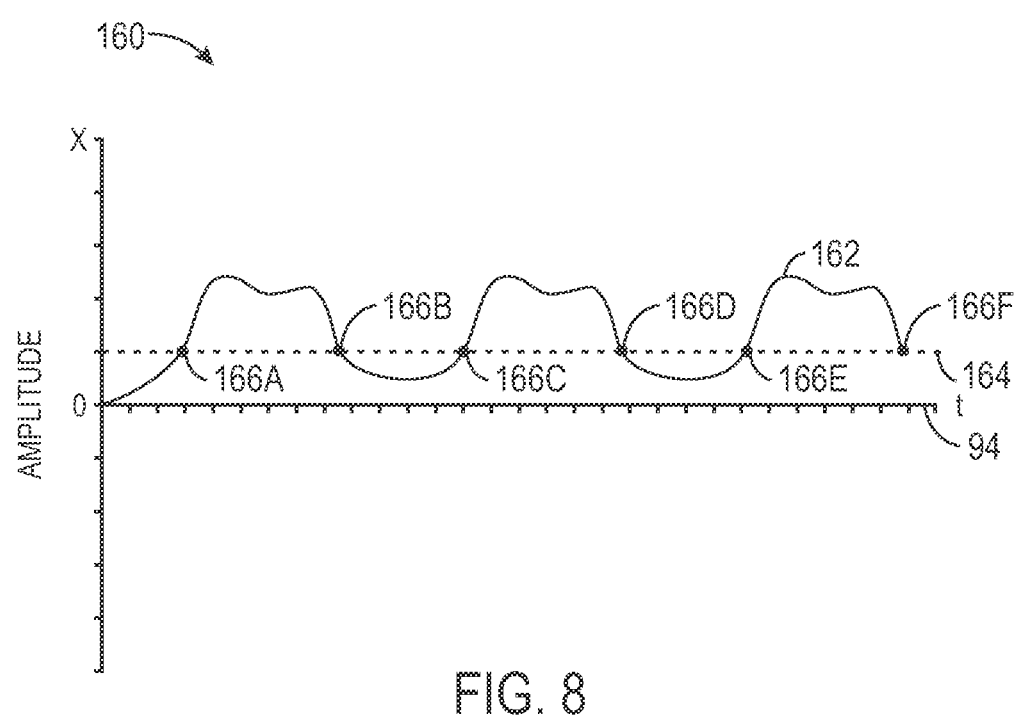
FIG. 8 illustrates an example of a pulse oximetry detector signal and a non-zero crossing, in accordance with an embodiment of the present disclosure.

As discussed above, the horizontal axis (e.g., the zero-boundary) is not the only horizontal boundary that may be used with the present technique. As such, FIG. 8 illustrates a plot 160 of a pulse oximetry detector signal 162, x, over time, t. The illustrated detector signal 162 intersects a horizontal boundary 164 (e.g., x=1) a number of times (e.g., intersections 166A-F). As such, as described above with regard to processes 120 and 140, the slope of the detector signal at each intersection (e.g., intersection 166A-F) may be determined (e.g., by taking the derivative of the detector signal at each intersection). Furthermore, the time between the intersections (e.g., intersections 166A-F), or the periodicity of the intersections, may be determined. As when the horizontal boundary is the zero-boundary (e.g., FIGS. 3-5), a processor may use the determined slopes of the detector signal at the intersections (e.g., intersections 166A-F) and the time between the intersections (e.g., intersections 166A-F) to estimate the quality of the detector signal (e.g., in process 140), estimate the amplitude of the detector signal (e.g., in process 120), or both. Accordingly, a processor may, in certain embodiments, use such an estimate of the amplitude of the detector signal to determine one or more physiological parameters of a patient (e.g., blood oxygen saturation and pulse rate).

APPENDIX A

```
% Author: Paul Addison
% Copyright Covidien 2011
function zerograd
close all
signalswitch=2
if signalswitch==1
siglen=10;
dt=.01;
sigt=[dt:dt:siglen];
P=2
A=1
fs1=1/P;
signal= A*sin(2*pi*fs1*sigt);
signal=signal';
sigt=[1:length(signal)]*dt;
random=0.0*rand(length(signal),1); signal=signal+random;figure;
else
siglen=10
dt=0.01
siglen=floor(siglen/dt)
A=1
P=1
CHR=60/P
pulselen=floor((60/CHR)/dt)
amps =A*[1,0.6,0.4]
gtimes=P*[0.2, 0.45 0.7]
sigmas=P*[0.08, 0.10, 0.12]
delay1=floor(gtimes(1)/dt);
delay2=floor(gtimes(2)/dt);
delay3=floor(gtimes(3)/dt);
AmpMult=1000
notchsig=zeros(3,siglen);
for i=delay1:pulselen:siglen
    notchsig(1,i)=amps(1);
end
for i=delay2:pulselen:siglen
    notchsig(2,i)=amps(2);
end
for i=delay3:pulselen:siglen
notchsig(3,i)=amps(3);
end
wholenotchsig=sum(notchsig);
figure; subplot(4,1,1); plot(wholenotchsig,'linewidth',3);
df=1/(dt*siglen);
f=zeros(1,siglen);
if length(f)/2==round(length(f)/2)
    f(1:round(length(f)/2)+1)=2.*pi.*[0:round(length(f)/2)].*df;
    f(round(length(f)/2)+2:end)=f(round(length(f)/2):-1:2);
else
    f(1:1+round((length(f)-1)/2))=2.*pi.*[0:round((length(f)-1)/2)].-*df;
    f(2+round((length(f)-1)/2):end)=f(1+round((length(f)-1)/2):-1:2);
```

APPENDIX A-continued

```
end
totalraw=[ ];
for j=1:3;
sigma=sigmas(j);
sig=notchsig(j,:);
gausplot=sqrt(2*pi).*sigma.*exp(-0.5.*((f).^2).*(sigma.^2));
rawfft=fft(sig).*(gausplot);
raw(j,:)=real(ifft(rawfft));
end
IR=raw;
p2p=max(-IR)-min(-IR);
subplot(4,1,2)
plot([0:length(IR)-1].*dt,IR,'linewidth',3);
sig=sum(raw);
sig=sig*AmpMult;
subplot(2,1,2);plot(sig,'linewidth',5);
save('pulsewave.mat', 'sig', 'dt', 'pulselen');
signal=sig';
subsamp=1
dt=dt*subsamp
signal=signal (subsamp:subsamp:end);
signal=signal(1: (floor(length(signal)/32) )*32);
siglen=length(signal); sigt=([1:siglen].*dt);signal=signal-mean(signal);
signal=signal-mean(signal);
end
figure;plot(sigt,signal,'linewidth',3)
hold on;plot(sigt, zeros(length(sigt),1),'k')
gradcrosses=[ ];gradtimes=[ ];gradcrossesneg=[ ];gradtimesneg=[ ];
gradcross=zeros(1, length(signal));
for i=1:length(signal)-1
if signal(i+1)>0 & signal(i)< 0
    gradcross(i)=(signal(i+1)-signal(i))/dt;
    gradcrosses=[gradcrosses, gradcross(i)];
    gradtimes=[gradtimes i*dt];
end
if signal(i+1)<0 & signal(i)> 0
    gradcross(i)=(signal(i+1)-signal(i))/dt;;
    gradcrosses=[gradcrosses, gradcross(i)];
    gradtimes=[gradtimes i*dt];
end
end
gradtimes
gradcrosses
difgradtimes=diff(gradtimes)
pers=difgradtimes*2 ;%gives one complete cycle
meanabsgrad=(abs(gradcrosses(2: end))+abs(gradcrosses(1: end-1)))/2
strength=pers.*meanabsgrad
```

What is claimed is:

1. A method for analyzing a detector signal of a physiological patient sensor, comprising:
   receiving the detector signal from the physiological patient sensor at a processor, wherein the detector signal crosses a horizontal boundary more than once;
   using the processor, determining a relative time and a slope of the detector signal at each point at which the detector signal crosses the horizontal boundary;
   using the processor, estimating an amplitude of the detector signal based, at least in part, on the determined relative time and slope of the detector signal at each point at which the detector signal crosses the horizontal boundary; and
   using the processor, determining a physiological parameter of a patient based, at least in part, on the estimate of the amplitude of the detector signal.

2. The method of claim 1, wherein the horizontal boundary is a zero boundary.

3. The method of claim 1, wherein determining the relative time of the detector signal at each point at which the detector signal crosses the horizontal boundary comprises determining the periodicity or the frequency of the points at which the detector signal crosses the horizontal boundary.

4. The method of claim 1, wherein determining the slope of the detector signal at each point at which the detector signal crosses the horizontal boundary comprises determining the derivative of the detector signal at each point at which the detector signal crosses the horizontal boundary.

5. The method of claim 1, wherein estimating the amplitude of the detector signal comprises multiplying values of the determined slopes of the detector signal at two adjacent points at which the detector signal crosses the horizontal boundary by the determined relative time between the two adjacent points.

6. The method of claim 1, wherein estimating the amplitude of the detector signal comprises estimating the amplitude of the detector signal using a probabilistic or stochastic method comprising non-parametric Bayesian estimates, neural networks, or any combination thereof.

7. The method of claim 1, wherein estimating the amplitude of the detector signal comprises estimating the amplitude of the detector signal using an adaptive rule-based system comprising propositional or predicate calculus, Modal, non-monotonic, or fuzzy logic, or any combination thereof.

8. The method of claim 1, wherein determining a physiological parameter of a patient comprises determining a pulse rate, oxygen saturation, respiration rate, respiration effort, continuous non-invasive blood pressure, cardiac output, fluid responsiveness, perfusion, pulse rhythm type, hydration level, or any combination thereof.

9. The method of claim 1, comprising displaying the physiological parameter on a display.

10. A patient monitoring system, comprising:
a patient monitor comprising:
an input configured to receive a detector signal from a physiological sensor; and
a processor configured to:
locate a portion of the detector signal between two adjacent intersections of the detector signal and a horizontal axis;
determine an amount of time between the two intersections of the detector signal and the horizontal axis;
determine a gradient for the detector signal at the two intersections of the detector signal and the horizontal axis; and
estimate the amplitude of the portion of the detector signal between the two intersections based, at least in part, on the determined amount of time between the two intersections and the determined gradients for the detector signal at the two intersections.

11. The system of claim 10, wherein the processor is configured to estimate the amplitude of the portion of the detector signal by multiplying mean, absolute values of the determined gradients of the two intersections by the amount of time between the two intersections.

12. The system of claim 10, wherein estimating the amplitude of the detector signal comprises estimating the amplitude of the detector signal using a probabilistic or stochastic method comprising non-parametric Bayesian estimates, neural networks, or any combination thereof.

13. The system of claim 10, wherein estimating the amplitude of the detector signal comprises estimating the amplitude of the detector signal using an adaptive rule-based system comprising propositional or predicate calculus, Modal, non-monotonic, or fuzzy logic, or any combination thereof.

* * * * *